US005739406A

United States Patent [19]

Pennetreau et al.

[11] Patent Number: 5,739,406
[45] Date of Patent: Apr. 14, 1998

[54] PROCESS FOR THE HYDROFLUORINATION OF CHLORO (FLUORO) BUTANE

[75] Inventors: Pascal Pennetreau, Rixensart; Francine Janssens, Vilvoorde, both of Belgium

[73] Assignee: Solvay (Société Anonyme), Brussels, Belgium

[21] Appl. No.: 520,763

[22] Filed: Aug. 30, 1995

[30] Foreign Application Priority Data

Sep. 5, 1994 [FR] France .................................. 94 10684

[51] Int. Cl.$^6$ .................................................. C07C 17/20
[52] U.S. Cl. ........................ 570/167; 570/165; 570/166; 570/168; 570/169
[58] Field of Search ............................ 560/167, 168, 560/165, 166, 169

[56] References Cited

U.S. PATENT DOCUMENTS

| | | |
|---|---|---|
| 2,439,299 | 4/1948 | Hovey et al. ............................ 570/168 |
| 2,981,762 | 4/1961 | Woolf . |
| 5,008,474 | 4/1991 | Wairaevens et al. .................... 570/168 |
| 5,347,059 | 9/1994 | Pennetreau et al. ..................... 570/166 |
| 5,395,997 | 3/1995 | Van Der Puy et al. ................. 570/166 |

FOREIGN PATENT DOCUMENTS

| | | | |
|---|---|---|---|
| 535808 | 1/1957 | Canada ................................... | 570/169 |
| 0522639 | 1/1993 | European Pat. Off. . | |
| 522638 | 1/1993 | European Pat. Off. ............... | 570/167 |
| 675372 | 7/1952 | United Kingdom . | |
| 938070 | 9/1963 | United Kingdom .................... | 570/167 |

OTHER PUBLICATIONS

E.T. McBee et al.: "Synthesis of Halobutanes". In: Ind. Eng. Chem. 39, 1947, pp. 418–420.

Primary Examiner—C. Warren Ivy
Assistant Examiner—Lyman H. Smith
Attorney, Agent, or Firm—Spencer & Frank

[57] ABSTRACT

Process for the hydrofluorination of chloro(fluoro)butane of general formula $C_4H_5Cl_xF_{5-x}$ in which x=1 to 5, by means of hydrogen fluoride and in the presence of a catalyst chosen from the derivatives of metals of groups IIIa, IVa, IVb, Va, Vb and VIb of the Periodic Table of the elements.

18 Claims, No Drawings

PROCESS FOR THE HYDROFLUORINATION OF CHLORO (FLUORO) BUTANE

The present invention relates to a process for the hydrofluorination of chloro(fluoro)butane of general formula $C_4H_5Cl_xF_{5-x}$ in which x=1 to 5. It also relates to the use of this process for the preparation of 1,1,1,3,3-pentafluorobutane.

McBee et al. (Ind. Eng. Chem., 39, 1947, p. 420) disclose a process for the preparation of 1,1,1,3,3-pentafluorobutane by hydrofluorination of 1,1,1-tri-chloro-3,3-difluorobutane by means of hydrogen fluoride in the presence of mercuric oxide. This known process for the preparation of 1,1,1,3,3-pentafluorobutane is difficult to exploit industrially, on the one hand because of the use of mercuric chloride and, on the other hand, because of the low yield of the hydrofluorination reaction (lower than 15%).

The objective of the present invention is to provide a process for hydrofluorination of chloro(fluoro)butane of general formula $C_4H_5Cl_xF_{5-x}$ in which x =1 to 5, which avoids the abovementioned disadvantages, which is simple to exploit industrially and which additionally makes it possible to reach a high degree of fluorination with a good hydrofluorination yield.

To this end, the invention relates to a process for the hydrofluorination of chloro(fluoro)butane of general formula $C_4H_5Cl_xF_{5-x}$ in which x =1 to 5, by means of hydrogen fluoride and in the presence of a catalyst chosen from derivatives of metals of groups IIIa, IVa, IVb, Va, Vb and VIb of the Periodic Table of the elements.

In the process according to the invention the expression chloro(fluoro)butane is intended to denote all the linear and branched compounds of general formula $C_4H_5Cl_xF_{5-x}$ in which x=1 to 5. The expression chloro(fluoro)butane accordingly incorporates both the pentachlorobutanes, the chlorofluorobutanes in accordance with the above formula and the mixtures of two or more of these compounds.

In a particular embodiment of the process according to the invention the chloro(fluoro)butane is selected from the compounds of general formula $CH_3-CCl_xF_{2-x}-CH_2-CCl_yF_{3-y}$ in which x=0, 1 or 2, y=0, 1, 2 or 3 and x+y ≧1. In this embodiment the chloro(fluoro)butane may especially include 1,1,1,3,3-pentachlorbutane $CH_3-CCl_2-CH_2-CCl_3$ or the following various chlorofluorobutanes: $CH_3-CCl_2-CH_2-CCl_2F$, $CH_3-CCl_2-CH_2-CClF_2$, $CH_3-CCl_2-CH_2-CF_3$, $CH_3-CClF-CH_2-CCl_3$, $CH_3-CClF, -CH_2-CCl_2F$, $CH_3-CClF-CH_2-CClF_2$, $CH_3-$ $CClF-CH_2-CF_3$, $CH_3-CF_2-$ $CH_2-CCl_3$, $CH_3-CF_2-CH_2-CCl_2F$ and $CH_3-CF_2-CH_2-CClF_2$, and the mixtures of these compounds with each other.

According to a first alternative form of this particular embodiment of the process the chloro(fluoro)butane is chosen from 1,1,3,3-tetrafluoro-1-chlorobutane, 1,3,3-trifluoro-1,1-dichlorobutane and 1,1,3-trifluoro-1,3-dichlorobutane.

According to another alternative form of this particular embodiment of the process according to the invention, use is made of chloro(fluoro)butane obtained by reaction of vinylidene chloride with hydrogen fluoride, for example a by-product of the industrial manufacture of 1-chloro-1,1-difluoroethane and/or of 1,1-dichloro-1-fluoroethane. In this alternative form of embodiment of the invention the chloro (fluoro)butane may contain other chlorinated or chlorofluorinated by-products, such as 1,1-dichloro-1-fluoroethane, 1,1,1-trichloroethane and chlorinated or chlorofluorinated hexanes. These impurities do not significantly impede the progress of the process according to the invention and can be separated subsequently from the reaction products obtained.

In the process according to the invention the catalyst is chosen from the derivatives of metals of groups IIIa, IVa, IVb, Va, Vb and VIb of the Periodic Table of the elements. Derivatives of metals of groups IIIa, IVa, IVb, Va, Vb and VIb of the Periodic Table of the elements are intended to mean the hydroxides, the oxides and the organic and inorganic salts of these metals, as well as their mixtures. The catalyst is preferably chosen from the derivatives of metals of groups IVa and Va of the Periodic Table of the elements, and more particularly from tin and antimony derivatives. In the process according to the invention the derivatives of metals of groups IIIa, IVa, IVb, Va, Vb and VIb of the Periodic Table of the elements are preferably salts and these are preferably chosen from the halides and more particularly from chlorides, fluorides and chlorofluorides. Catalysts which are particularly preferred according to the present invention are tin and antimony chlorides, fluorides and chlorofluorides, especially tin tetrachloride and antimony pentachloride. Antimony pentachloride is very particularly preferred.

The quantity of catalyst used may vary within wide limits. It is generally at least 0.001 mole of catalyst per mole of chloro(fluoro)butane. It is preferably at least 0.01 mole of catalyst per mole of chloro(fluoro)butane. In most cases the quantity of catalyst used does not exceed 1 mole of catalyst per mole of chloro(fluoro)butane. It preferably does not exceed 0.1 mole of catalyst per mole of chloro(fluoro) butane.

The molar ratio of hydrogen fluoride to the chloro (fluoro)butane used is generally at least 4. The work is preferably done with a molar ratio of at least 8. The molar ratio of hydrogen fluoride to the chloro(fluoro)butane used generally does not exceed 25. It is preferable that the molar ratio should not exceed 18.

The temperature at which the hydrofluorination is performed is generally at least 50° C. It is preferably at least 80° C. The temperature generally does not exceed 150° C. It preferably does not exceed 130° C. In the case where the catalyst employed is antimony pentachloride the best results are obtained at a temperature of at least 100° C. In the case where the catalyst employed is tin tetrachloride the best results are obtained at a temperature of at least 120° C.

The process according to the invention is preferably carried out in liquid phase. In this case the pressure is chosen so as to keep the reaction mixture in liquid form. The pressure used varies as a function of the temperature of the reaction mixture. It is generally from 2 bar to 40 bar.

The process according to the invention may be carried out in any reactor made of a material which resists the temperature, the pressure and the reactants employed, especially hydrogen fluoride.

The process according to the invention may be carried out noncontinuously or continuously. In this latter case it is advantageous to separate the product obtained from the reaction mixture and to recycle the other reactants and products to the reactor, especially the incompletely fluorinated chloro(fluoro)butane fraction.

The process may be carried out in a closed or open system. In this latter case it is advantageous to extract, wholly or partly, the hydrogen chloride formed from the reaction mixture. In such a technique it is possible, for example, to implement the process in a boiling reactor supporting a rectification column in order to complete the separation between hydrogen chloride and the other products.

The process according to the invention finds an advantageous application in the preparation of 1,1,1,3,3- pentafluorobutane by hydrofluorination of chloro(fluoro)butane of general formula $CH_3-CCl_xF_{2-x}-CH_2-CCl_yF_{3-y}$ in which x=0, 1 or 2, y=0, 1, 2 or 3 and x+y≧1. In this application of the process according to the invention the hydrofluorination catalyst is advantageously chosen from the inorganic salts (preferably chlorides, fluorides and chlorofluorides) of metals of groups IVa and Va of the Periodic Table of the elements. The duration of the hydrofluorination reaction which is needed to ensure an optimum yield of 1,1,1,3,3-pentafluorobutane can vary as a function of the operating conditions and can be evaluated by laboratory tests in each particular case. At the end of the hydrofluorination reaction the 1,1,1,3,3-pentafluorobutane produced can be recovered with ease. An advantageous operating method in the laboratory consists in cooling the reactor to ambient temperature and transferring its content into a separating funnel filled with water and tetrachloroethylene. The organic phase containing 1,1,1,3,3-pentafluorobutane is next separated from the aqueous phase which contains particularly the unreacted hydrogen fluoride. The 1,1,1,3,3-pentafluorobutane can be subsequently purified by distillation.

The examples which follow are given with the aim of illustrating the invention but do not imply any limitation.

EXAMPLE 1

A 0.5-1 autoclave made of Hastelloy® B2 stainless steel was employed, equipped with a stirrer, a temperature probe, a bursting disc, a dip tube enabling the sampling of liquid phase to be performed during the tests and an entry allowing reactants to be introduced.

This reactor, evacuated and cooled to −20° C. beforehand, was charged with 109 g of a mixture containing 73.2% by weight of $CH_3-CF_2-CH_2-CClF_2$ and 19.2% by weight of a compound of empirical formula $C_4H_5Cl_2F_3$, the remainder (7.6% by weight) consisting of 1,1-dichloro-1-fluoroethane, trichloroethane and chlorofluorinated hexanes. 0.036 moles of tin tetrachloride and 7.25 moles of hydrogen fluoride were added to it in succession.

The reaction mixture was stirred and was then gradually heated to 100° C. and the pressure was adjusted to 20 bar. After 4 hours at 100° C. the temperature was increased to 120° C.

The progress of the hydrofluorination reaction was followed using sampling carried out at regular intervals in the liquid phase. These samples were diluted in tetrachloroethylene and their composition was determined by vapour phase chromatographic analysis. The result of these analyses is repeated in Table I.

TABLE I

| DURATION (1) | COMPOSITION % mole/mole C4 (2) | | |
|---|---|---|---|
| hours | $C_4H_5Cl_2F_3$ | $CH_3-CF_2-CH_2-CClF_2$ | $CH_3-CF_2-CH_2-CF_3$ |
| initial mixture | 21 | 79 | 0 |
| 0 | 11 | 88 | 1 |
| 0.5 | 4 | 93 | 3 |
| 1 | 2 | 94 | 4 |
| 2 | 1 | 94 | 5 |
| 4 | 0.5 | 92 | 7.5 |
| 5.5 | 0 | 85 | 15 |
| 6.5 | 0 | 70 | 30 |
| 7.5 | 0 | 48 | 52 |
| 8.5 | 0 | 37.5 | 62.5 |
| 10.5 | 0 | 21 | 79 |

(1) duration starting from the time when the temperature in the reactor has reached 100° C.
(2) mole C4 = sum of the molar fractions of the compounds $C_4H_5Cl_2F_3$, $CH_3-CF_3-CH_2-CClF_2$ and $CH_3-CF_2-CH_2-CF_3$.

The results in Table I show that, in the presence of tin tetrachloride, at 120° C., the formation of 1,1,1,3,3-pentafluorobutane reaches a yield close to 80% after 6 h of reaction.

EXAMPLE 2

The procedure was similar to that of Example 1.

The reactor, evacuated and cooled to −20° C. beforehand, was charged with 127 g of a mixture containing 2.4% by weight of $CH_3-CF_2-CH_2-CClF_2$ and 90.3% by weight of a compound of empirical formula $C_4H_5Cl_2F_3$, the remainder (7.3% by weight) including 1,1-dichloro-1-fluoroethane, trichloroethane and chlorofluorinated hexanes. 0.042 moles of antimony pentachloride and 8.45 moles of hydrogen fluoride were added to it in succession.

The reaction mixture was stirred and was then gradually heated to 100° C. and the pressure was adjusted to 20 bar.

The progress of the hydrofluorination reaction was followed by sampling carried out at regular intervals in the liquid phase. These samples were diluted in tetrachloroethylene and their composition was determined by vapour phase chromatographic analysis. The result of these analyses is repeated in Table II.

TABLE II

| DURATION (1) | COMPOSITION % mole/mole C4 (2) | | |
|---|---|---|---|
| hours | $C_4H_5Cl_2F_3$ | $CH_3-CF_2-CH_2-CClF_2$ | $CH_3-CF_2-CH_2-CF_3$ |
| initial mixture | 97 | 3 | 0 |
| 0 | 15 | 66 | 19 |
| 0.5 | <0.5 | 62 | 38 |
| 1 | 0 | 52 | 48 |
| 2 | 0 | 43 | 57 |
| 4 | 0 | 34 | 66 |
| 6 | 0 | 31 | 69 |

(1) duration starting from the time when the temperature in the reactor has reached 100° C.
(2) mole C4 = sum of the molar fractions of the compounds $C_4H_5Cl_2F_3$, $CH_3-CF_2-CH_2-CClF_2$ and $CH_3-CF_2-CH_2-CF_3$.

The results in Table II show that in the presence of antimony pentachloride, at 100° C., the formation of 1,1,1,3,3-pentafluorobutane is fast, with a yield of approximately 70% after 6 h of reaction.

EXAMPLE 3

The procedure used was analogous to that of Example 2. The reactor, evacuated and cooled to −20° C. beforehand, was charged with 124 g of a mixture containing 2.4% by weight of $CH_3$-$CF_2$-$CH_2$-$CClF_2$ and 90.3% by weight of a compound of empirical formula $C_4H_5Cl_2F_3$, the remainder (7.3% by weight) including 1,1-dichloro-1-fluoroethane, trichloroethane and chlorofluorinated hexanes. 0.041 moles of antimony pentachloride and 8.2 moles of hydrogen fluoride were added to it in succession.

The reaction mixture was stirred and was then gradually heated to 120° C. and the pressure was adjusted to 20 bar.

The results of the chromatographic analyses are repeated in Table III.

TABLE III

| DURATION (1) | COMPOSITION % mole/mole C4 (2) | | |
|---|---|---|---|
| hours | $C_4H_5Cl_2F_3$ | $CH_3-CF_2-CH_2-CClF_2$ | $CH_3-CF_2-CH_2-CF_3$ |
| initial mixture | 97 | 3 | 0 |
| 0 | 0 | 25 | 75 |
| 0.5 | 0 | 7 | 93 |
| 1 | 0 | 3 | 97 |
| 2 | 0 | 1 | 99 |
| 4 | 0 | <0.5 | >99.5 |

(1) duration starting from the time when the temperature in the reactor has reached 120° C.
(2) mole C4 = sum of the molar fractions of the compounds $C_4H_5Cl_2F_3$, $CH_3-CF_2-CH_2-CClF_2$ and $CH_3-CF_2-CH_2-CF_3$.

The results in Table III show that in the presence of antimony pentachloride, at 120° C., the hydrofluorination reaction is very fast, with a yield of 1,1,1,3,3-pentafluorobutane that is higher than 90% after 0.5 h of reaction. The reaction is virtually complete (99%) after 2 h of reaction.

We claim:

1. A process for the preparation of 1,1,1,3,3-pentafluorobutane by hydrofluorination of chloro(fluoro)butane of general formula $CH_3CCl_xF_{2-x}$-$CH_2$-$CCL_yF_{3-y}$ in which x=0, 1 or 2, y=0, 1, 2 or 3 and x+y≧1, by means of hydrogen fluoride, comprising performing the hydrofluorination in the presence of a catalyst selected from the group consisting of the derivatives of metals of groups IVa, IVb, Va, and Vb of the Periodic Table of the elements, at a temperature from 80° C. to 130° C.

2. The process according to claim 1, wherein the catalyst is selected from the group consisting of the derivatives of metals of groups IVa and Va of the Periodic Table of the elements.

3. The process according to claim 2, wherein the catalyst is selected from the group consisting of tin and antimony derivatives.

4. The process according to claim 1, wherein the catalyst is selected from the group consisting of chlorides, fluorides and chlorofluorides.

5. The process according to claim 4, wherein the catalyst is antimony pentachloride.

6. The process according to claim 1, comprising using the catalyst in a proportion of 0.001 to 1 mole of catalyst per mole of chloro(fluoro)butane.

7. The process according to claim 1, wherein the molar ratio of hydrogen fluoride to the chloro(fluoro)butane used is from 4 to 25.

8. The process according to claim 1, wherein the hydrofluorination is carried out in liquid phase at a pressure of 2 bar to 40 bar.

9. The process according to claim 1, wherein the chloro(fluoro)butane is selected from 1,1,3,3-tetrafluoro-1-chlorobutane, 1,3,3-trifluoro-1,1-dichlorobutane and 1,1,3-trifluoro-1,3-dichlorobutane.

10. The process according to claim 1, comprising reacting vinylidene chloride with hydrogen fluoride to obtain said chloro(fluoro)butane.

11. A process for the preparation of 1,1,1,3,3-pentafluorobutane by hydrofluorination of 1,1,1,3,3-pentachlorobutane by means of hydrogen fluoride, comprising performing the hydrofluorination in the presence of a catalyst chosen from the derivatives of metals of groups IVa, IVb, Va, and Vb of the Periodic Table of the elements, at a temperature from 80° C. to 130° C.

12. The process according to claim 11, wherein the catalyst is selected from the group consisting of derivatives of metals of Groups IVa and Va of the Periodic Table of the Elements.

13. The process according to claim 12, wherein the catalyst is selected from the group consisting of tin and antimony derivatives.

14. The process according to claim 11, wherein the catalyst is selected from the group consisting of chlorides, fluorides, and chlorofluorides.

15. The process according to claim 14, wherein the catalyst is antimony pentachloride.

16. The process according to claim 11, wherein said catalyst is in a proportion of 0.001 to 1 mole of catalyst per mole of chloro(fluoro)butane.

17. The process according to claim 11, wherein the molar ratio of hydrogen fluoride to the chloro(fluoro)butane used is from 4 to 25.

18. The process according to claim 11, wherein the hydrofluorination is carried out in liquid phase at a pressure of 2 bar to 40 bar.

* * * * *